United States Patent
Tucker (10) Patent No.: US 10,398,799 B2
(45) Date of Patent: Sep. 3, 2019

(54) SYSTEM FOR DISINFECTING CONTACT LENSES

(71) Applicant: Novartis AG, Basel (CH)

(72) Inventor: Robert Carey Tucker, Suwanee, GA (US)

(73) Assignee: Novartis AG, Basel (CH)

(*) Notice: Subject to any disclaimer, the term of this patent is extended or adjusted under 35 U.S.C. 154(b) by 273 days.

(21) Appl. No.: 15/300,296

(22) PCT Filed: Mar. 23, 2015

(86) PCT No.: PCT/US2015/021946
§ 371 (c)(1),
(2) Date: Sep. 29, 2016

(87) PCT Pub. No.: WO2015/153159
PCT Pub. Date: Oct. 8, 2015

(65) Prior Publication Data
US 2017/0182201 A1    Jun. 29, 2017

Related U.S. Application Data

(60) Provisional application No. 61/974,574, filed on Apr. 3, 2014.

(51) Int. Cl.
*A61L 12/02* (2006.01)
*A61L 12/12* (2006.01)
(Continued)

(52) U.S. Cl.
CPC ........... *A61L 12/124* (2013.01); *A61L 12/023* (2013.01); *A61L 12/10* (2013.01); *B08B 3/08* (2013.01);
(Continued)

(58) Field of Classification Search
None
See application file for complete search history.

(56) References Cited

U.S. PATENT DOCUMENTS

| 4,011,941 A | 3/1977 | Parsons |
| 4,585,488 A | 4/1986 | Giefer |

(Continued)

FOREIGN PATENT DOCUMENTS

| EP | 0124461 A1 | 11/1984 |
| GB | 1484945 | 9/1977 |

(Continued)

OTHER PUBLICATIONS

International Search Report and Written Opinion of the International Searching Authority, dated Jun. 5, 2015, International Application No. PCT/US2015/021946, International Filing Date: Mar. 23, 2015; 10 Pages

(Continued)

*Primary Examiner* — Stefanie S Wittenberg
(74) *Attorney, Agent, or Firm* — Jian Zhou (57) ABSTRACT

The present invention is generally directed to a hydrogen peroxide-based lens care system for disinfecting contact lenses. Unlike hydrogen peroxide-based system known in the prior art, a lens care system of the present invention involves electrochemically neutralizing of hydrogen peroxide after any desired period of disinfection time for which contact lenses have been immersed in a hydrogen peroxide-based lens care solution.

19 Claims, 3 Drawing Sheets

(51) Int. Cl.

| | | |
|---|---|---|
| *B08B 3/08* | (2006.01) | |
| *C02F 1/461* | (2006.01) | |
| *C02F 1/66* | (2006.01) | |
| *A61L 12/10* | (2006.01) | |
| *C11D 3/00* | (2006.01) | |
| *C11D 3/39* | (2006.01) | |
| *C11D 11/00* | (2006.01) | |

(52) U.S. Cl.
CPC ............... *C02F 1/461* (2013.01); *C02F 1/66* (2013.01); *C11D 3/0078* (2013.01); *C11D 3/3947* (2013.01); *C11D 11/007* (2013.01); *C02F 2201/46115* (2013.01); *C02F 2307/02* (2013.01)

(56) References Cited

U.S. PATENT DOCUMENTS

| | | |
|---|---|---|
| 4,637,919 A | 1/1987 | Ryder |
| 4,748,992 A | 6/1988 | Giefer |
| 4,750,610 A | 6/1988 | Ryder |
| 4,776,360 A | 10/1988 | Ching |
| 4,812,173 A | 3/1989 | Tsao |
| 4,816,232 A | 3/1989 | Barrau |
| 4,836,859 A | 6/1989 | Konishi |
| 4,852,591 A | 8/1989 | Wisotzki |
| 4,889,689 A | 12/1989 | Tsao |
| 4,899,914 A | 2/1990 | Schweigl |
| 4,956,156 A | 9/1990 | Kanner |
| 4,986,290 A | 1/1991 | Oguma |
| 4,996,027 A | 2/1991 | Kanner |
| 5,011,661 A | 4/1991 | Schäfer |
| 5,089,240 A | 2/1992 | Perlaky |
| 5,117,849 A | 6/1992 | Zimmerli |
| 5,196,174 A | 3/1993 | Cerola |
| 5,225,055 A | 7/1993 | Sibley |
| 5,250,266 A | 10/1993 | Kanner |
| 5,252,291 A | 10/1993 | Tsao |
| 5,275,784 A | 1/1994 | Perlaky |
| 5,302,345 A | 4/1994 | Oksman |
| 5,312,586 A | 5/1994 | Stockel |
| 5,314,590 A | 5/1994 | Kamiya |
| 5,320,806 A | 6/1994 | Dziabo |
| 5,451,303 A | 9/1995 | Heiler |
| 5,462,713 A | 10/1995 | Schlitzer |
| 5,468,448 A | 11/1995 | Nicolson |
| 5,487,788 A | 1/1996 | Kamiya |
| 5,523,012 A | 6/1996 | Winterton |
| 5,558,846 A | 9/1996 | Alvord |
| 5,576,028 A | 11/1996 | Martin |
| 5,591,397 A | 1/1997 | Schlitzer |
| 5,609,264 A | 3/1997 | Cerny |
| 5,609,837 A | 3/1997 | Cerny |
| 5,807,585 A | 9/1998 | Martin |
| 5,958,351 A | 9/1999 | Cerny |
| 6,183,705 B1 | 2/2001 | Chang |
| 6,440,411 B2 | 8/2002 | Scherer |
| 6,945,389 B2 | 9/2005 | Scherer |
| 7,022,654 B2 | 4/2006 | Tsao |
| 8,318,144 B2 | 11/2012 | Ketelson |
| 8,329,098 B2 | 12/2012 | Kanner |
| 2002/0194852 A1 | 12/2002 | Furuta et al. |
| 2008/0276971 A1 | 11/2008 | Ifejika |
| 2010/0233023 A1 | 9/2010 | Kanner |
| 2011/0114517 A1 | 5/2011 | Minick |
| 2012/0152284 A1 | 6/2012 | Winterton |
| 2012/0205255 A1 | 8/2012 | Roster |
| 2014/0158623 A1* | 6/2014 | Pudil ................ A61M 1/1656 210/647 |

FOREIGN PATENT DOCUMENTS

| | | | |
|---|---|---|---|
| GB | 1484972 | | 9/1977 |
| GB | 2094992 A | | 9/1982 |
| JP | 63254417 | * | 10/1988 ............ G02C 13/00 |
| JP | 2286163 A | | 11/1990 |
| JP | 05095991 | * | 4/1993 ............... A61L 2/18 |
| JP | 2669690 B2 | | 10/1997 |
| JP | H1152309 A | | 2/1999 |
| WO | 9534327 A1 | | 12/1995 |
| WO | 2012/083089 A2 | | 6/2012 |
| WO | 2013056165 A1 | | 4/2013 |

OTHER PUBLICATIONS

Celine Coulon, Anne Collignon, Gerald McDonnell and Vincent Thomas, Resistance of Acanthamoeba Cysts to Disinfection Treatments Used in Health Care Settings, Journal of Clinical Microbiology, 2010, vol. 48, No. 8, pp. 2689-2697.

L. Czarnetzki and L. J. J. Janssen, Electrochemical Oxidation of Hypochlorite at Platinum Anodes, Electrochimica Acta., 1988, vol. 33, No. 4, pp. 561-566.

L. R. Czarnetzki and L. J. J. Janssen, Formation of hypochlorite, chlorate and oxygen during NaCl electrolysis from alkaline solutions at an $RuO_2/TiO_2$ anode, Journal of Applied Electrochemistry, 1992, vol. 22, pp. 315-324.

Reanne Hughes and Simon Kilvington, Comparison of Hydrogen Peroxide Contact Lens Disinfection Systems and Solutions against Acanthamoeba polyphaga, Antimicrobial Agents and Chemotherapy, 2001, vol. 45, No. 7, pp. 2038-2043.

Stephanie P. Johnston, Rama Sriram, Yvonne Qvarnstrom, Sharon Roy, Jennifer Verani, Jonathan Yoder, Suchita Lorick, Jacquelin Roberts, Michael J. Beach and Govinda Visvesvara, Resistance of Acanthamoeba Cysts to Disinfection in Multiple Contact Lens Solutions, Journal of Clinical Microbiology, 2009, vol. 47, No. 7, pp. 2040-2045.

N. Krstajic, V. Nakic, M. Spasojevic, Hypochlorite Production. I. A model of the cathodic reactions, Journal of Applied electrochemistry, 1987, vol. 17, pp. 77-81.

Yoshiharu Mukouyama, Shuji Nakanishi, Hidemitsu Konishi, Kouhei Karasumi and Yoshihiro Nakato, Observation of two stationary states of low and high $H_2O_2$-reduction currents at a Pt electrode, arising from the occurrence of a positive feedback mechanism including solution-stirring by gas evolution, Phys. Chem. Chem. Phys., 2001, vol. 3, pp. 3284-3289.

S Patra and N Munichandraiah, Electrochemical reduction of hydrogen peroxide on stainless steel, J. Chem. Sci., 2009, vol. 121, No. 5, pp. 675-683.

\* cited by examiner

SYSTEM FOR DISINFECTING CONTACT LENSES

BACKGROUND OF THE INVENTION

*Acanthamoeba* is a genus of amoeba most commonly found in most soil and water habitats and can form metabolically inactive cysts which are resistant to desiccation, temperature fluctuation from −20 to 56° C., and most disinfectants at working concentrations. It can cause *acanthamoeba keratitis*, a painful, potentially-blinding infection of the cornea. *Acanthamoeba keratitis* is often associated with trauma to the cornea and with contact lens wear as a result of poor lens care and hygiene.

It has been reported that hydrogen peroxide-based lens care solutions can be effective against the resistant cyst form of *Acanthamoeba* when being used at a concentration of 3% with an exposure time of at least 4 to 6 hours. See, S. P. Johnston et al., "Resistance of *Acanthamoeba* cysts to disinfection in multiple contact lens solutions," Journal of clinical microbiology, vol. 47, no. 7, pp. 2040-5, July (2009); R. Hughes & S. Kilvington, "Comparison of Hydrogen Peroxide Contact Lens Disinfection Systems and Solutions against *Acanthamoeba polyphaga*," Antimicrobial Agents and Chemotherapy, vol. 45, no. 7, pp. 2038-2043, July 2001. However, hydrogen peroxide in these lens care systems is toxic to the cornea and thereby must be neutralized before lenses can safely be worn by a patient. Hydrogen peroxide typically is neutralized by adding a catalyst either during the disinfection process (i.e., one-step involving use of a platinum-coated disk or soluble catalase tablet) or afterward (i.e., two-step involving the addition of a catalase or a reducing agent after a designated disinfection time), for example, as described in patents and published patent applications U.S. Pat. Nos. 4,585,488, 4,748,992, 4,899,914, 5,011,661, 6,440,411, 5,089,240, 5,196,174, 5,275,784, 5,468,448, 5,558,846, 5,609,264, 5,609,837, 5,958,351, 6,945,389, 4,812,173, 4,889,689, 5,523,012, 5,576,028, 5,807,585, 5,462,713, 5,591,397, 5,312,586, US 2011/0114517, and EP0124461 (herein incorporated by references in their entireties). The study of Hughes and Kilvington indicated that the commercially available hydrogen peroxide-based, one-step lens care systems has low or no activity against the cysts of *Acanthamoeba* species under study because of insufficient exposure time, whereas the commercially available two-step systems can have at least a 3-log kill after 4 hours of exposure. However, one disadvantage associated with the use of a two-step system is that a patient may inadvertently fail to neutralize hydrogen peroxide or prematurely remove lenses from the system, thereby suffering pain and trauma caused by hydrogen peroxide introduced into the eye.

WO 2013056165 describes a complicated lens cleaning system which functions as a two-step hydrogen peroxide system while, for the user, it functions as a one-step system. A system of WO 2013056165 comprises a reservoir for holding a hydrogen peroxide solution, a complex base that is coupled to the reservoir to ensure a hermetically closed reservoir environment and has a first and a second segment, a lens holder assembly configured to locate and releasably coupled lenses within the reservoir and being coupled to the first segment, and a drive mechanism being coupled to the second segment and configured to selectively introduce a catalyst to the hydrogen peroxide solution.

U.S. Pat. No. 4,836,859 describes a method for treating contact lenses with hydrogen peroxide involving electrochemically decomposing and removing the remaining hydrogen peroxide. However, this patent fails to address issues associated with electrolysis of hydrogen peroxide solutions, such as, for examples, pH changes, by-products (e.g., chlorine, hypochlorite, etc.) of electrolysis of hydrogen peroxide solution, etc.

U.S. Pat. No. 5,225,055 describes an aqueous solution for use in electrochemical cleaning and disinfecting contact lenses, which comprises hydrogen peroxide, a blend of sodium chloride (as a first ionizable salt) and second ionizable salt including a metal of Group IA or IIA of the Periodic Table.

U.S. Pat. No. 5,302,345 describes a method of and apparatus for generating superoxides and other free radicals for cleaning and sterilizing contact lenses, tonometers and other poorly oxidizing objects in an electrolytic solution which may optionally include an antiseptic such as hydrogen peroxide, enzymes and soaps and for neutralizing the above agents by using electrolysis to decompose the peroxide and to generate free radicals that neutralize the enzymes and soaps and sterilize. However, this patent does not address the left-over free radicals generated for neutralizing the enzymes and soaps and for sterilizing lenses.

Thus, there is still a need for a simple lens care systems which can have microbial efficacy toward a broad spectrum of organisms including *Acanthameoba*.

SUMMARY OF THE INVENTION

Generally described, the present invention is related to a method and a lens care system for disinfecting contact lenses, which can be effective against a broad spectrum of organisms including *Acanthameoba*.

The invention, in one aspect, provides a method for disinfecting and cleaning contact lenses which are suitable for direct insertion into the eye upon completion of disinfection. A method of the invention comprises the steps of: (1) immersing a contact lens in an aqueous lens care solution including about 0.5% to about 6% by weight (preferably about 2% to about 6% by weight, more preferably from about 3% and about 4% by weight) of hydrogen peroxide for a predetermined period of immersing time (preferably at least about one hour, more preferably from about 2 hour to about 6 hours, even more preferably from about 3 hours to about 5 hours) sufficient to disinfect the contact lens, wherein the aqueous lens care solution comprises from about 0.30% to about 1.4% (preferably from about 0.5% to about 1.2%, more preferably from about 1.0%) by weight of one or more chloride salts (e.g., sodium chloride, potassium chloride, or both) and has a pH of from about 6 to about 8 (preferably from about 6.5 to about 7.5, more preferably from about 6.8 to about 7.2) and a tonicity of from about 150 to about 400 mOsm/kg (preferably from about 200 to about 350 mOsm/kg, more preferably from about 250 to about 350 mOsm/kg) as measured by osmolality at 25° C. of the solution according to any known method; and (2) after the predetermined period of immersing time, electrochemically neutralizing said hydrogen peroxide in the aqueous lens care solution with the contact lens immersed therein so as to reduce the concentration of hydrogen peroxide to less than 20 ppm (preferably about 10 ppm or less, more preferably about 5 ppm or less, even more preferably about 1 ppm or less) without electrolytic formation of chlorine and/or hypochlorite, wherein the step of electrochemically neutralizing the hydrogen peroxide is carried out by using an anode having a ion selective membrane (ISM) thereon so as to prevent chloride ions from approaching the electrode to form chlorine and/or hypochlorite, wherein the step of electrochemically neutralizing the hydrogen peroxide does not cause a change in pH (i.e., $\Delta pH=|pH_o-pH_f|$, in which $pH_o$ is the initial pH of the lens care solution and $pH_f$ is the final pH of the lens care solution after electrochemical neutralization of hydrogen peroxide) of the aqueous lens care solution being greater than about 1.0 (preferably greater than about 0.5).

In another aspect, the present invention relates to a lens care system (i.e., apparatus) for disinfecting and cleaning contact lenses, comprising: a container for holding a hydrogen peroxide-based lens care solution having a pH of from about 6 to about 8 (preferably from about 6.5 to about 7.5, more preferably from about 6.8 to about 7.2) and comprising from about 0.30% to about 1.4% (preferably from about 0.5% to about 1.2%, more preferably from about 1.0%) by weight of one or more chloride salts (e.g., sodium chloride, potassium chloride, or both) and a tonicity of from about 150 to about 400 mOsm/kg (preferably from about 200 to about 350 mOsm/kg, more preferably from about 250 to about 350 mOsm/kg) as measured by osmolality at 25° C. of the solution according to any known method; one pair of electrodes for electrochemically neutralizing hydrogen peroxide in the hydrogen peroxide-based lens care solution, wherein the pair of electrodes consists of one cathode and one anode having an ion selective membrane (ISM) thereon so as to prevent chloride ions from approaching the electrode to form chlorine and/or hypochlorite and to electrolytically cause a change in pH (i.e., $\Delta pH=|PH_o-pH_f|$, in which $pH_o$ is the initial pH of the lens care solution and $pH_f$ is the final pH of the lens care solution after electrochemical neutralization of hydrogen peroxide) of the aqueous lens care solution not being greater than about 1.0 (preferably greater than about 0.5); and a control unit operatively connected to the electrodes and to a power source for automatically controlling the electrode polarity and potential of the electrodes, as well as the timing and duration of electrochemically neutralizing of hydrogen peroxide, so that optimum disinfection and cleaning efficacy is obtained, wherein the container comprises a container cup defining an interior chamber accessible through an opening bounded by a rim and for receiving the hydrogen peroxide-based lens care solution, a cap for removable attachment onto the container cup to cover the opening, and a lens holder for retaining the contact lenses immersed in the hydrogen peroxide-based lens care solution in the container cup, wherein the electrodes are located in the interior chamber and immersed in the hydrogen peroxide-based lens care solution when in use.

These and other aspects, features and advantages of the invention will be understood with reference to the figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EMBODIMENTS OF THE INVENTION

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well-known and commonly employed in the art. Also, as used in the specification including the appended claims, reference to singular forms such as "a," "an," and "the" include the plural, and reference to a particular numerical value includes at least that particular value, unless the context clearly dictates otherwise. "About" as used herein means that a number referred to as "about" comprises the recited number plus or minus 1-10% of that recited number.

The present invention is directed to a hydrogen peroxide-based lens care system for disinfecting contact lenses. Unlike hydrogen peroxide-based system known in the prior art, a lens care system of the present invention relies on the electrochemical neutralization of hydrogen peroxide without electrolytic formation of chlorine and/or hyperchlorite and without altering significantly the pH of the hydrogen peroxide based lens care solution. The following electrolysis half-reactions may occur in an aqueous hydrogen peroxide solution.

At Anode $$H_2O_2 \rightarrow O_2 + 2H^+ + 2e^- \tag{1}$$

$$2Cl^- \rightarrow Cl_2 + 2e^- \tag{2}$$

$$2H_2O \rightarrow O_2 + 4H^+ + 4e^- \tag{3}$$

At Cathode $$H_2O_2 + 2H^+ + 2e^- \rightarrow 2H_2O \tag{4}$$

$$H_2O_2 + 2e^- \rightarrow 2OH^- \tag{5}$$

$$2H_2O + 2e^- \rightarrow 2H_2 + 2OH^- \tag{6}$$

By eliminating or minimizing the electrolysis reaction (2), the pH of the hydrogen peroxide solution may be likely maintained (i.e., a change in pH, $\Delta pH=|pH_o-pH_f|$ in which $pH_o$ is the initial pH of the solution and $pH_f$ is the final pH of the solution after electrochemical neutralization of hydrogen peroxide) during electrolysis of hydrogen peroxide. Furthermore, by eliminating or minimizing the electrolysis reaction (2), one can also eliminate or minimize the formation of undesirable by-products including chlorine and hypochlorite, because those undesirable by-products during electrochemical neutralization of hydrogen peroxide could adversely affect the cornea health (e.g., damaging the ocular region).

One of the advantages of this system is that hydrogen peroxide can be allowed to disinfect lenses for any desired period of time so as to kill even resistant cyst form of *Acanthamoeba* and then conveniently neutralized electrochemically. For example, a concentrated peroxide solution (e.g., about 3% by weight) initially can be used to disinfect contact lenses for a desired period of time (e.g., about 2 hours or more). Once this desired period of time for disinfection is complete, then a current can be applied to a pair of electrodes (e.g., platinum electrodes) which electrochemically neutralize hydrogen peroxide into water.

Another advantage of this system is its simplicity, high controllability, ease of implementation, and relatively low cost, because it is based on a simple electrochemistry and can be implemented and controlled by using a pair of electrodes, a power source and a control means for turning-on and off the electric current.

A lens care system of the invention can be used to disinfect any contact lenses including hard (PMMA) contact lenses, soft (hydrophilic) contact lenses, and rigid gas permeable (RGP) contact lenses. The soft contact lenses are hydrogel contact lens or silicone hydrogel contact lenses.

A "hydrogel" refers to a polymeric material which can absorb at least 10 percent by weight of water when it is fully hydrated. Generally, a hydrogel material is obtained by polymerization or copolymerization of at least one hydrophilic monomer in the presence or absence of additional monomers and/or macromers.

A "silicone hydrogel" refers to a hydrogel obtained by copolymerization of a polymerizable composition comprising at least one silicone-containing vinylic monomer or at least one silicone-containing macromer.

"Hydrophilic," as used herein, describes a material or portion thereof that will more readily associate with water than with lipids.

For the purposes of the present invention the term "disinfect" means the rendering non-viable of substantially all pathogenic microorganisms including *Acanthameoba*.

The invention, in one aspect, provides a method for disinfecting and cleaning contact lenses which are suitable for direct insertion into the eye upon completion of disinfection. A method of the invention comprises the steps of: (1) immersing a contact lens in an aqueous lens care solution including about 0.5% to about 6% by weight (preferably about 2% to about 6% by weight, more preferably from about 3% and about 4% by weight) of hydrogen peroxide for a predetermined period of immersing time (preferably at least about one hour, more preferably from about 2 hour to about 6 hours, even more preferably from about 3 hours to about 5 hours) sufficient to disinfect the contact lens, wherein the aqueous lens care solution comprises from about 0.30% to about 1.4% (preferably from about 0.5% to about 1.2%, more preferably from about 0.8% to about 1.0%) by weight of one or more chloride salts (e.g., sodium chloride, potassium chloride, or both) and has a pH of from about 6 to about 8 (preferably from about 6.5 to about 7.5, more preferably from about 6.8 to about 7.2) and a tonicity of from about 150 to about 400 mOsm/kg (preferably from about 200 to about 350 mOsm/kg, more preferably from about 250 to about 350 mOsm/kg) as measured by osmolality at 25° C. of the solution according to any known method; and (2) after the predetermined period of immersing time, electrochemically neutralizing said hydrogen peroxide in the aqueous lens care solution with the contact lens immersed therein so as to reduce the concentration of hydrogen peroxide to less than 20 ppm (preferably about 10 ppm or less, more preferably about 5 ppm or less, even more preferably about 1 ppm or less) without electrolytic formation of chlorine and/or hypochlorite, wherein the step of electrochemically neutralizing the hydrogen peroxide is carried out by using an anode having a ion selective membrane (ISM) thereon so as to prevent chloride ions from approaching the electrode to form chlorine and/or hypochlorite, wherein the step of electrochemically neutralizing the hydrogen peroxide causes a change in pH, designated as $\Delta pH$, of about 1.0 or less (preferably about 0.5 or less), wherein $\Delta pH = |pH_o - pH_f|$ in which $pH_o$ is the initial pH of the lens care solution and $pH_f$ is the final pH of the lens care solution after electrochemical neutralization of hydrogen peroxide.

A person skilled in the art knows well how to adjust the tonicity of an aqueous solution with a tonicity agent. Besides chloride salts (e.g., sodium chloride and potassium chloride), other suitable occularly acceptable tonicity agents known to a person skilled in the art can be used in adjusting the tonicity of the lens care solution. Preferred examples of other tonicity agents include, without limitation, sodium sulfate, potassium sulfate, glycerol, propylene glycol, polyethylene glycols, polios, mannitols, sorbitol, xylitol and mixtures thereof.

An aqueous lens care solution of the invention is formulated to have a pH within a physiologically acceptable range of from about 6.0 to about 8.0, preferably from about 6.5 to about 7.5, more preferably from about 6.8 to about 7.2. The pH of the aqueous lens care solution of the invention preferably comprises one or more buffer selected from inorganic or organic bases, preferably basic acetates, phosphates, borates, citrates, nitrates, sulfates, tartrates, lactates, carbonates, bicarbonates and mixtures thereof, more preferably basic phosphates, borates, citrates, tartrates, carbonates, bicarbonates and mixtures thereof. Typically, it is present in an amount of 0.001% to 2%, preferably 0.01% to 1%; most preferably from about 0.05% to about 0.30% by weight. The buffer capacity can also be modified to minimize changes in pH.

The buffer component preferably includes one or more phosphate buffers, for example, combinations of monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$), and potassium monobasic phosphate ($KH_2PO_4$).

In accordance with the invention the aqueous lens care solution preferably further comprises a surfactant for cleaning the contact lens. Any suitable known surfactants can be used in the invention. Examples of suitable surfactants include, but are not limited to homopolymers of polyethylene glycol or polyethyleneoxide, poloxamers under the tradename Pluronic from BASF Corp. (Pluronic™ and Pluronic-R™) which are nonionic surfactants consisting of block copolymers of propylene oxide and ethylene oxide; poloxamine which is a block copolymer derivative of ethylene oxide and propylene oxide combined with ethylene diamine; tyloxapol, which is 4-(1,1,3,3-tetramethylbutyl) phenol polymer with formaldehyde and oxirane; ethoxylated alkyl phenols, such as various surface active agents available under the tradenames TRITON (Union Carbide, Tarrytown, N.Y., USA) and IGEPAL (Rhone-Poulenc, Cranbury, N.J., USA); polysorbates such as polysorbate 20, including the polysorbate surface active agents available under the tradename TWEEN (ICI Americas, Inc., Wilmington, Del., USA.); alkyl glucosides and polyglucosides such as products available under the tradename PLANTAREN (Henkel Corp., Hoboken, N.J., USA); and polyethoxylated castor oils commercially available from BASF under the trademark CREMAPHOR; and combinations thereof.

Preferred surfactants include polyoxypropylene-polyoxyethylene-polyoxypropylene block copolymers, poly(oxyethylene)-poly(oxybutylene) block copolymers disclosed in U.S. Pat. No. 8,318,144 (incorporated herein by reference in its entirety), certain poloxamers such as materials commercially available from BASF under the tradenames PLURONIC® surfactants, and combinations thereof. Examples of PLURONIC® surfactants include: PLURONIC® L42, PLURONIC® L43, and PLURONIC® L61. Examples of PLURONIC® R surfactants include: PLURONIC® 31R1, PLURONIC® 31R2, PLURONIC® 25R1, PLURONIC® 17R1, PLURONIC® 17R2, PLURONIC® 12R3, PLURONIC® 17R4, PLURONIC® F-68NF, PLURONIC® F68LF, and PLURONIC® F127. Examples of poly(oxyethylene)-poly(oxybutylene) block copolymers include di-block copolymer, denoted as PEO-PBO (i.e., polyoxyethylene-polyoxybutylene), a tri-block copolymer, represented as PEO-PBO-PEO or PBO-PEO-PBO, or other block-type configurations. When present, surfactants may be employed at a concentration of from about 0.005% to about 1% by weight, preferably from about 0.01% to about 0.5% by weight, more preferably from about 0.02% to about 0.25% by weight, even more preferably from about 0.04% to about 0.1% by weight, based on the total amount of aqueous lens care solution.

In a preferred embodiment, an aqueous lens care solution of the invention further comprises a polyoxypropylene-polyoxyethylene-polyoxypropylene block copolymer in an amount of from about 0.005% to about 1% by weight, preferably from about 0.01% to about 0.5% by weight, more preferably from about 0.02% to about 0.25% by weight, even more preferably from about 0.04% to about 0.1% by weight, based on the total amount of aqueous lens care solution.

In another preferred embodiment, an aqueous lens care solution of the invention further comprises a poly(oxyethylene)-poly(oxybutylene) block copolymer, in an amount of from about 0.005% to about 1% by weight, preferably from about 0.01% to about 0.5% by weight, more preferably from about 0.02% to about 0.25% by weight, even more preferably from about 0.04% to about 0.1% by weight, based on the total amount of aqueous lens care solution.

As used in this application, a poly(oxyethylene)-poly(oxybutylene) block copolymer may be in the form of a di-block copolymer, denoted as PEO-PBO, a tri-block copolymer, represented as PEO-PBO-PEO or PBO-PEO-PBO, or other block-type configurations.

In accordance with this preferred embodiment, the poly(oxyethylene)-poly(oxybutylene) block copolymers utilized in the present invention have a weight average molecular weight in the range of from about 400 to about 1200 Daltons; and more preferably in the range of from about 700 to about 900 Daltons.

In another preferred embodiment, an aqueous lens care solution of the invention further comprises a homopolymer or copolymer of vinylpyrrolidone, in an amount of from about 0.02% to about 5% by weight, preferably 0.1 to 3%; more preferably from about 0.5% to about 2%, most preferably from about 0.25% to about 1.5% by weight, based on the total amount of aqueous lens care solution.

In accordance with this preferred embodiment of the invention, any copolymers of vinylpyrrolidone and at least one hydrophilic monomer can be used in this invention. A preferred class of copolymers is the copolymers of vinyloyrrolidone and at least one amino-containing vinylic monomer. Examples of amino-containing vinylic monomers include without limitation alkylaminoalkylmethacrylate having 8-15 carbon atoms, alkylaminoalkylacrylate having 7-15 carbon atoms, dialkylaminoalkylmethacrylate having 8-20 carbon atoms, dialkylaminoalkylacrylate having 7-20 carbon atoms, N-vinylalkylamide having 3-10 carbon atoms. Examples of preferred N-vinyl alkylamide include without limitation N-vinyl formaide, N-vinyl acetamide, N-vinyl isopropylamide, and N-vinyl-N-methyl acetamide. Examples of preferred copolymers includes without limitation copolymers of vinylpyrrolidone and dimethylaminoethylmethacrylate. Such preferred copolymers are commercially available, e.g., Copolymer 845 and Copolymer 937 from ISP.

An aqueous lens care solution of the invention may contain a hydrogen peroxide stabilizer. Preferably, the stabilizer is a diphosphonic acid alkanol as disclosed in U.S. Pat. No. 4,812,173. The most preferred stabilizer is diethylene triamine penta-(methylenephosphonic acid) or a physiologically compatible salt thereof. This compound is manufactured by Solutia under the name DEQUEST® 2060. The stabilizer is preferably present in the solution in an amount between about 0.001 and about 0.03% by weight of the composition, and most preferably between about 0.006 and about 0.0120% by weight of the solution. Stabilization of hydrogen peroxide in contact lens disinfection systems is described in more detail in U.S. Pat. Nos. 4,812,173 and 4,889,689, both incorporated herein by reference.

If desired, additional conventional stabilizers may be employed in conjunction with or in place of the diethylene triamine penta-(methylenephosphonic acid) if it is compatible with the material to be sterilized. Some conventional stabilizers are not compatible with the polymers typically found in contact lenses (e.g., sodium stannate), and should therefore, only be used with materials which would not be adversely affected by stannate stabilizers.

An aqueous lens care solution of the invention is preferably formulated in such a way that it has a viscosity of about 0.8 centipoise to about 15 centipoises at 25° C., preferably from about 0.8 centipoises to about 10 centipoises at 25° C., more preferably from about 0.8 centipoises to about 1.1 centipoises at 25° C. It is known to a person skilled in the art how to adjust the viscosity of an aqueous solution by using one or more viscosity-enhancing agents.

In accordance with the invention, an aqueous lens care solution of the invention can further comprise from about 0.002% to about 0.5% by weight, more preferably from about 0.004% to about 0.1% by weight, even more preferably from about 0.005% to about 0.05% by weight of one or more components selected from the group consisting of lubricant(s), conditioning/wetting agent(s), chelating agent(s), defoaming agents, microbicide(s), preservative(s), and combinations thereof, based on the total amount of aqueous lens care solution.

A lens care solution of the invention preferably comprises a lubricant. "Lubricants" as used herein refer to any compounds or materials which can enhance surface wettability of a contact lens and/or the eye or reduce the friction character of the contact lens surface. Examples of lubricants include without limitation mucin-like materials and hydrophilic polymers.

Exemplary mucin-like materials include without limitation polyglycolic acid, polylactides, collagen, and gelatin. A mucin-like material may be used to alleviate dry eye syndrome. The mucin-like material preferably is present in effective amounts.

Exemplary hydrophilic polymers include, but are not limited to, polyvinylalcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methaacrylamide, a copolymer of acrylamide or methacrylamide with one or more hydrophilic vinylic monomers, mixtures thereof.

An aqueous lens care solution of the invention can also comprise one or more conditioning/wetting agents (e.g., polyvinyl alcohol, polyoxamers, polyvinyl pyrrolidone, hydroxypropyl cellulose, and mixture thereof).

An aqueous lens care solution of the invention may include (but preferably does not include) an effective amount of a chelating agent. Any suitable, preferably ophthalmically acceptable, chelating agents may be included in the present compositions, although ethylenediaminetetraacetic acid (EDTA), salts thereof and mixtures thereof are particularly effective. EDTA is low level non-irritating chelating agent and can be synergistic with PHMB to increase antimicrobial efficacy. Typical amount of EDTA is from about 0.002% to about 0.5% by weight, more preferably from about 0.004% to about 0.1% by weight, even more preferably from about 0.005% to about 0.05% by weight, based on the total amount of aqueous lens care solution.

An aqueous lens care solution of the invention is produced in known manner, in particular, by means of conventional mixing of the constituents with water or dissolving the constituents in water.

One or more contact lenses can be disinfected with a contact lens care apparatus comprising a contact lens container (which comprises a container cup, a cap for removable attachment onto the container cup, a lens holder for retaining the contact lenses immersed in a hydrogen peroxide solution in the container cup) and a pair of electrodes immersed in the hydrogen peroxide solution for neutralizing hydrogen peroxide. Containers used in lens care systems are known in the art, and examples are provided in U.S. Pat. Nos. 4,011,941, 4,637,919, 4,750,610, 4,956,156, 4,966,027, 5,089,240, 5,196,174, 5,250,266, 5,275,784, 5,468,448, 5,558,846, 5,609,264, 5,609,837, 5,958,351, 6,945,389, 8,329,098 and US published patent application No. 2012/0152284 A1, the disclosures of which are incorporated herein by references in their entireties. The contact lens containers utilized in such lens care systems typically comprise closable baskets, which open to receive the contact lenses to be cleaned and close to retain the lenses during treatment. The baskets are typically part of a contact lens holder component, which in turn can be connected to the cap of a contact lens container. Before the cap is placed onto the container cup, the container cup is dosed to a fill level with a hydrogen peroxide lens care solution. Finally, the contact lens holder containing the lenses to be treated is immersed into the hydrogen peroxide solution in the container cup, and the container is closed by screwing the cap onto the container cup. The closure of the cap on the container cup may form a water-tight seal, to prevent leakage of the cleaning solution. The contact lenses are allowed to remain immersed in the solution for a period of time sufficient to complete the specified cleaning and/or disinfecting process. The oxygen produced from decomposition of hydrogen peroxide in the cleaning solution typically must be allowed to discharge from the container in some manner, e.g., according to one of various known gas discharge mechanisms, such as those disclosed in U.S. Pat. Nos. 4,011,941, 4,637,919, 4,750,610, 4,956,156, 4,966,027, 5,196,174, 5,250,266, 5,558,846, 5,609,264, 5,609,837, 5,958,351, 6,945,389, 8,329,098 and US published patent application No. 2012/0152284 (incorporated herein by reference in their entireties).

Containers known in the art can be modified to contain two electrodes (anode with an ISM thereon and cathode), which are spaced apart from each other but preferably is as close as possible to each other. In one preferred embodiment, the two electrodes (anode and cathode) are separated merely by an ISM to facilitate movement of protons between the two electrodes. The electrodes are comprised of a conventional inert electrically conductive material, e.g. platinum, graphite, palladium, aluminum, gold, silver, ruthenium, or boron doped diamond, or a conductive polymer. Preferably, catalytic electrodes, such as, platinum, silver, ruthenium, or boron doped diamond, are used in the invention to accelerate the neutralization of hydrogen peroxide.

The contact lens care apparatus of the present invention also includes a control unit (means), operatively connected to the electrodes and to a power source. The control unit permits the control of the polarity of each electrode and the amount of potential voltage applied to each electrode. Preferably the control unit is automatic and controls the electrode polarity and potential voltage according to a predetermined program. Preferably, the control unit also includes means (e.g., one or more miniaturized electronic devices, such as microprocessors and/or embedded systems, as known to a person skilled in the art) for automatically controlling the electrode polarity and potential of the electrodes, as well as the timing and duration of the electrochemical neutralization process, so that the optimum disinfection and cleaning efficacy is obtained. The control unit may optionally contain a power pack (AC-DC converter or a battery), an automatic switching mechanism, indicator means, etc.

The lens care apparatus may be designed so that it is turned on by the user using a hand-operated switching device. Alternatively, the apparatus may be automatically activated, for example, upon closing (attaching) of the container cap onto the container cup.

Figure 1:
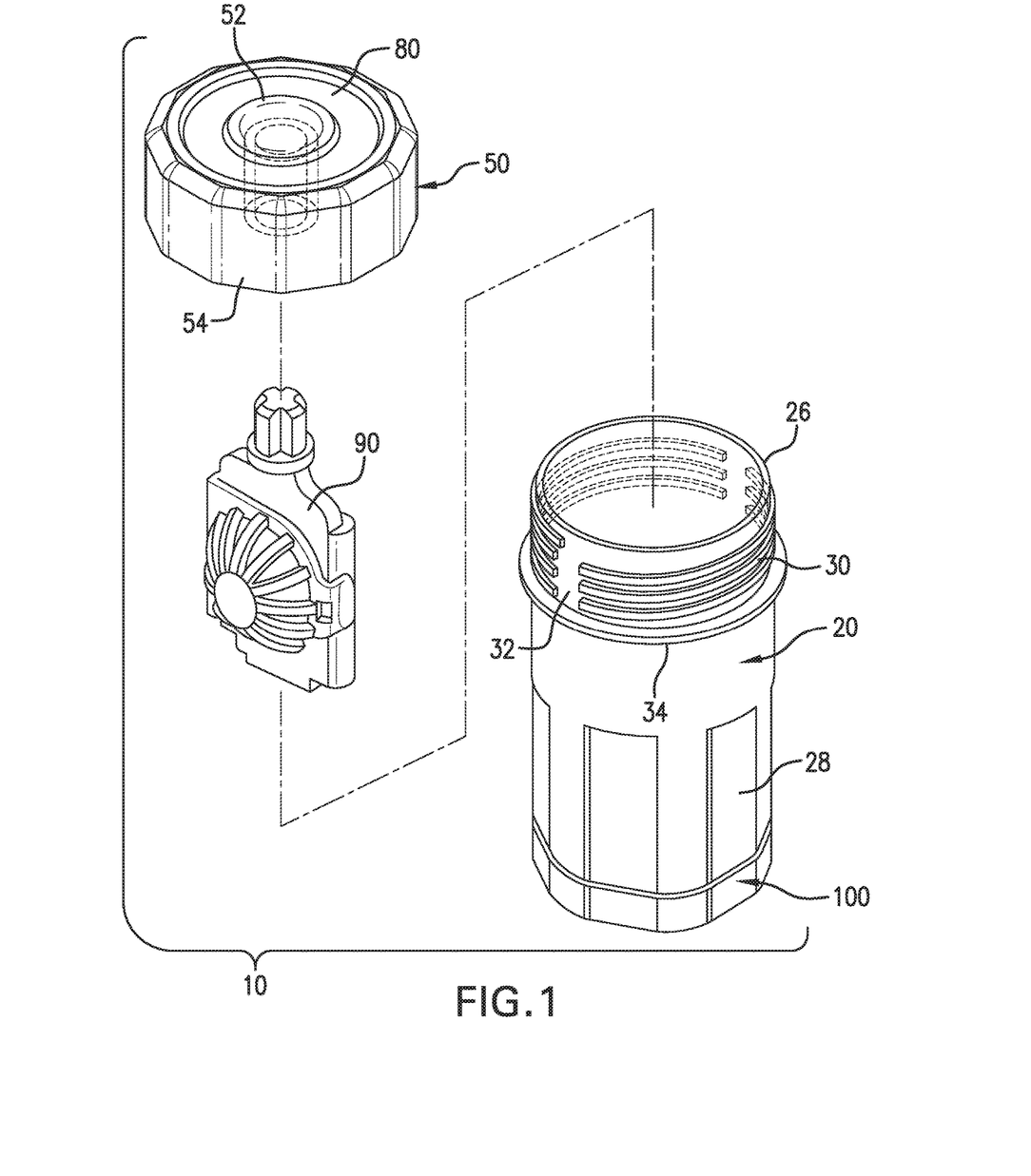
FIG. 1 is an assembly view of a lens care apparatus according to a preferred embodiment of the present invention.
Figure 2:
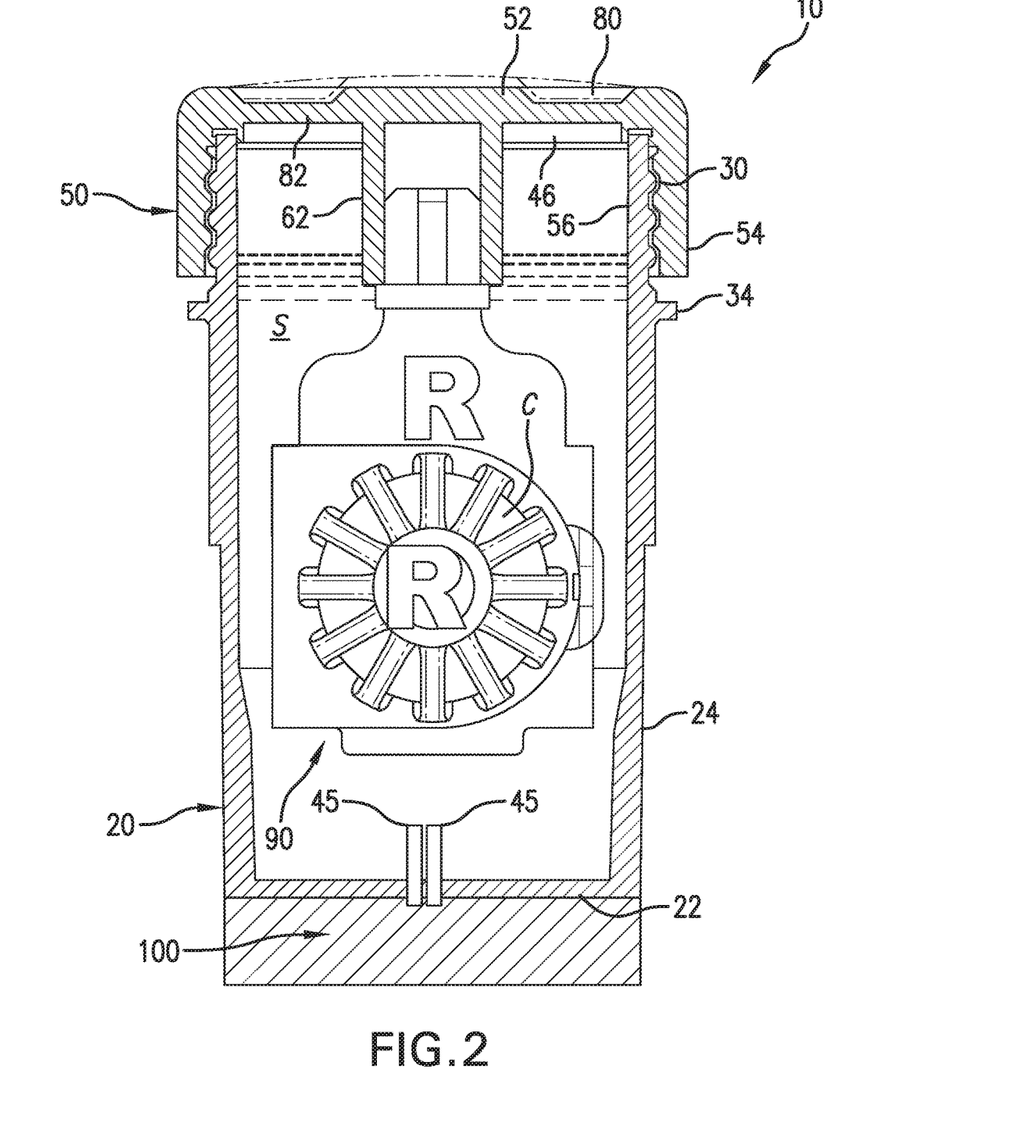
FIG. 2 is a cross-sectional view of the lens care apparatus of FIG. 1 in an assembled state.

FIGS. 1 and 2 illustrate a preferred apparatus 10 for cleaning, disinfecting and/or storing one or more contact lenses or other ophthalmic or medical devices. The lens care apparatus 10 generally comprises a container cup 20, a cap 50 for removable attachment onto the container cup, a lens holder 90, and a control unit 100. FIG. 1 shows the components in a partially disassembled state; whereas FIG. 2 shows the assembled apparatus in an example manner of use, with a contact lens C retained in the lens holder 90 and immersed in a liquid lens care solution S, and with the pair of electrodes 45 operatively connected to the control unit 100 and immersed in the liquid lens care solution S.

The container cup 20 is generally cylindrical, having a bottom panel 22 and a tubular sidewall 24 having a generally circular profile. The container cup defines an interior chamber accessible from an open top end bounded by a circumferential upper rim 26 opposite the bottom panel 22. One or more flats 28 or other surface features are optionally provided on the exterior surface of the sidewall 24 to provide improved grip for a user.

Two electrodes 45 are provided on the bottom panel 22 and are spaced to each other spaced apart from each other but preferably as close as possible to each other. In one preferred embodiment, the two electrodes 45 are separated merely by an ISM to facilitate movement of protons between the two electrodes. Any conventional inert electrically conductive material, e.g. platinum, graphite, palladium, aluminum, gold, silver, ruthenium, or boron doped diamond, or a conductive polymer, can be used in making the electrodes 45. Preferably, catalytic electrodes, such as, platinum, silver, ruthenium, or boron doped diamond, are used in the invention to accelerate the neutralization of hydrogen peroxide. More preferably, the electrodes 45 comprise an ion selective membrane (ISM) thereon so as to prevent chloride ions from approaching the electrode to form undesirable electrolytic products, such as chlorine and hyperchlorite. A negatively charged ISM such as Nafion can be used in this invention. It is understood that a liquid-tight seal should be formed between the electrodes 45 and the bottom panel 22 of the container cup.

Alternatively, the two electrodes can be attached to the bottom of the lens holder 90 and protrude downwardly from the lens holder 90.

The control unit 100 comprises means (e.g., electronic circuitry) (not shown) for operatively connecting the electrodes with the power source (not shown) and microprocessors/embedded systems (not shown) for automatically controlling the electrode polarity and potential of the electrodes, as well as the timing and duration of the electrochemical neutralization process. The control unit 100 preferably also contains a power pack (AC-DC covnerter or a C battery), an automatic switching mechanism, indicator means, etc. (not shown). The control unit 100 may be a separate unit from the container cup 20 and they may be connected to each other by cable or an interlocking socket arrangement. Alternatively, the control unit 100 may be permanently incorporated in the container cup 20 as an integral part of the bottom panel 22.

The container cup 20 is preferably a unitary component, for example integrally molded of polystyrene, polypropylene, polyethylene, ABS and/or other plastic or polymeric material(s) of construction, as by injection molding or other fabrication process. The container cup 20 comprises a first helical thread profile 30 on its exterior surface proximal the upper rim 26. The first threads 30 are optionally split by one or more unthreaded segments 32, providing a discharge channel for gas vented from the container during use, as will be described below. The unthreaded segment 32 preferably defines a gas venting channel extending generally linearly from the rim 26 of the container cup through the entire threaded portion of the cup, providing a passage for free discharge flow of pressurized gas therethrough from the container when the cap is assembled onto the cup. A circumferential cup flange 34 extends transversely outward from the exterior surface of the sidewall 24 beneath the thread profile 30.

The cap 50 comprises a generally circular top panel 52 and a circumferential collar 54 extending transversely downward from the top panel. The collar 54 has an inner diameter configured to receive the outer diameter of the container cup 20, preferably with a loose or free running fit. The interior face of the collar 54 comprises a second helical thread profile 56, which engages with the first thread profile 30 on the container cup 20 when the cap 50 is screwed onto the container cup to hold the components together in their assembled state. The second threads 56 are optionally split by one or more unthreaded segments, providing a discharge channel for gas vented from the container during use. Also, sufficient spacing or play is preferably provided between the first and second thread profiles to permit gas discharge through the threaded interface. The collar 54 optionally comprises one or more flats along its exterior circumference, forming a rounded polygonal profile, to provide improved grip for a user. The cap 50 is preferably a unitary component, for example integrally molded of polypropylene, polyethylene, polystyrene, ABS and/or other plastic or polymeric material(s) of construction, as by injection molding or other fabrication process.

A coupling hub 62 projects downward from the center of the interior face of the top panel 52 of the cap 50, and defines a central receiver for receiving a cooperating retention finger of the lens holder 90. A resilient cap sealing flange or lip 46 projects downward from the interior face of the top panel 52 of the cap 50. The lip 46 has a continuous circular profile extending proximal the outer periphery of the interior face of the top panel 52, and spaced inwardly from the threaded interior face of the collar 54 a distance generally corresponding to the wall thickness of the sidewall 24 of the container cup 20. In this manner, when the cap 50 is installed onto the container cup 20, the outer face of the lip 46 interfaces with the interior surface of the container cup along its rim 26 to form a continuous liquid-tight seal in the cap's undeformed state. The outer face of the lip 46 is optionally provided a slight inward taper, to provide a ring of sealing point contact at the edge formed by the intersection of the upper face of the rim 26 and the interior surface of the container cup. The lip 46 is preferably an integral part of the cap 50, rather than a separate component, such that a sealing and venting interface is formed between the cup and the cap with minimal complexity. In this manner, no separate washer or seal component is required to form a seal between the container cup and the cap. In alternate embodiments, the seal interface comprises separate seal and/or vent components attached to the cap and/or cup.

A spaced array of interference ribs (not shown) are optionally provided along the interior face of the top panel 52 between the lip 46 and the interior face of the collar 54, to prevent tightening the cap 50 to such an extent that the rim 26 of the container cup 20 would seal against the interior face of the cap's top panel to prevent discharge of gas from the container. Alternatively, one or more recesses can be formed in the interior face of the top panel between the cap's lip and the interior face of its collar to allow gas discharge. Seating of the interference ribs on the interior face of the cap's top panel against the rim 26 of the container cup 20 defines the position of the cap relative to the container cup when the container is closed, and this seating location is controlled to provide a specified degree of interference or compression between the tapered contact face of the cap's sealing lip 46 against the container cup's rim. For example, control of the diameter of the sealing lip 46 and the height of the interference ribs to provide a seal interference of about 25 μm-50 μm between the sealing lip of the cap with the rim of the container cup may provide a suitable releasable seal interface.

The top panel 52 of the cap 50 has an annular channel or ring-shaped recess or depression 80 formed in its upper or exterior surface. This channel 80 results in a circular section or web 82 of decreased material thickness around the periphery of the top panel 52. The outer periphery of the section of reduced thickness 82 on the exterior surface of the top panel 52 is generally aligned with and opposite the position of the sealing lip 46 on the interior surface of the top panel. The material of construction of the cap 50 and the thickness and location of this section 82 are specified in conjunction to result in a top panel 52 configuration that allows a degree of flexure of the top panel in response to a threshold pressure within the container. For example, the cap 50 may comprise a polypropylene such as Huntsman/FHR P5M6K-048 polymer, and the web 82 of decreased material thickness have a thickness of between about 0.75 mm-1.75 mm, for example about 1.25 mm, and a diametral span of about 20 mm-30 mm, for example about 25 mm. When a threshold pressure of for example 1-8 pounds per square inch (psi) is reached, the top panel deforms or bulges outwardly from its undeformed state (shown in solid lines in FIG. 2B) into a deformed state (shown in broken lines in FIG. 2B), causing the lip 46 to tilt inwardly and out of contact with the rim 26 of the container cup. Pressurized gas within the contained volume defined by the cup 20 and attached cap 50 may then escape or vent through the threaded interface of the cup and cap, and/or though the gas venting channel formed by the unthreaded segment 32 of the threaded coupling between the container cup and the cap, if present. Because no separate seal or washer component is interposed between the container cup and the cap, the released gas discharges directly between the cap and the container cup, without passing through any intermediate seal chamber or cavity. Release of the excess gas reduces the pressure within the contained volume back below the threshold pressure, and the top panel returns to its undeformed state biased by the cap material's resilience or shape memory. During the cleaning and disinfecting process, continuing gas generation may result in an intermittent sequence or cycle of increasing pressure and venting or "burping" to release excess gas. The resilience of the cap 50 maintains the circular lip 46 of the cap 50 in sealing contact with the rim 26 of the container cup 20 except when venting excess gas, thereby preventing leakage of liquid from the container. In alternate embodiments, the top panel of the cap comprises various other configurations allowing for controlled flexure or deformation and release of excess internal pressure. For example, a recessed section could be formed on the interior and/or exterior surface(s) of the top panel, a plurality of ribs of varying flexure may be formed on the top panel, and/or a series of stepped indentations or rings may be formed on the top panel.

Figure 3:
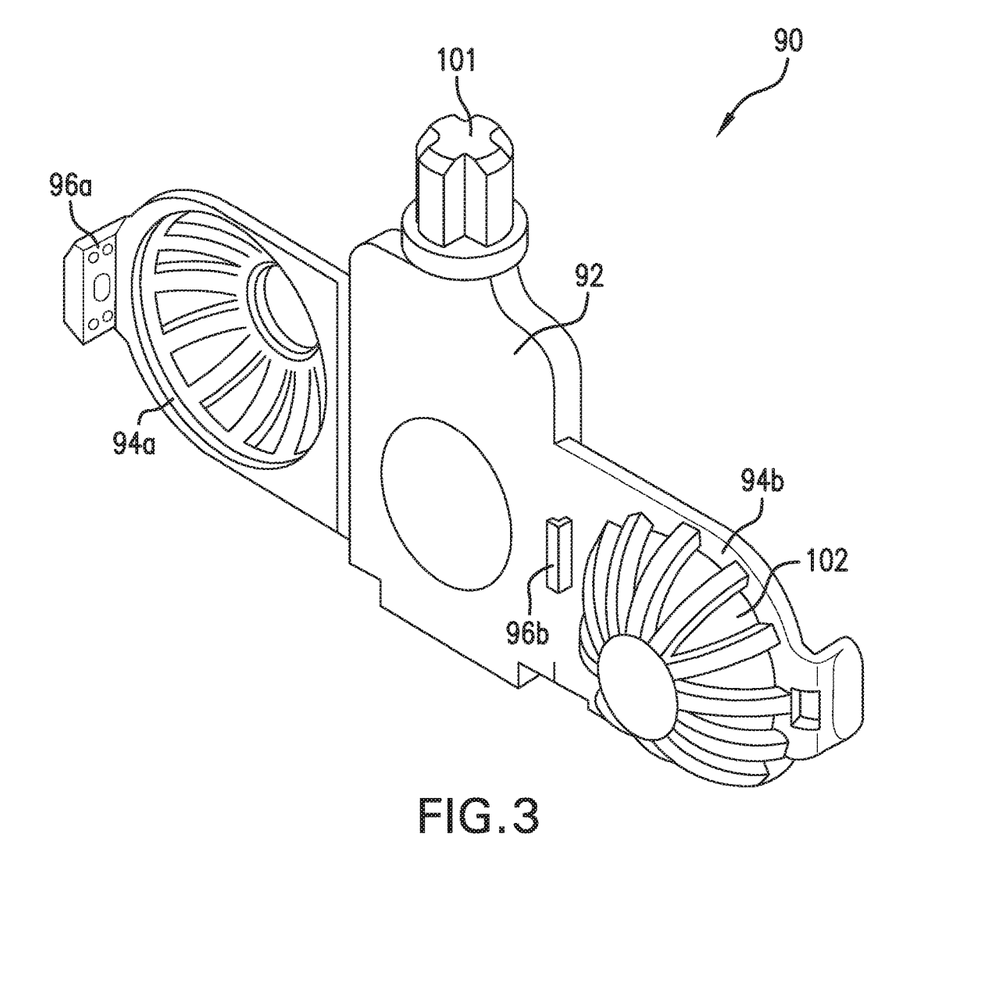
FIG. 3 is a perspective view of the contact lens holder component of the lens care apparatus of FIG. 1, with its lens retaining baskets shown in an open configuration.

The lens holder 90 is shown in detail in its open state in FIG. 3. The lens holder comprises a body panel 92 having first and second lens basket panels 94a, 94b attached thereto by an integral or living hinge formed by a web of reduced material thickness. Interengaging clips or closure members 96a, 96b are provided for holding the lens basket panels in their closed state, and releasing with finger pressure to allow insertion and removal of a lens from the basket. A retention finger 101 extends from an upper end of the body panel 92. The retention finger 101 optionally define a cross-shaped profile for stability. The retention finger 101 has an outer periphery configured to form an interference or clearance fit within the receiver of the coupling hub 62 of the cap 50 as shown in FIG. 2. The basket panels 94 are perforated with a plurality of slots or openings 102 to allow lens care solution to flow therethrough.

In use, the container 10 is opened by unscrewing the cap 50 from the container cup 20. A liquid such as a hydrogen peroxide based lens care solution is dispensed into the container cup to a desired fill level. One or more contact lenses are placed in the lens holder 90 between the body panel and the basket panels, and the basket panels are closed and clasped. The retention finger of the lens holder is inserted into the receiver of the cap's hub. The lens holder and lenses are inserted into the container cup and immersed in the lens care solution. The cap is screwed onto the container cup to close the container, bringing the sealing lip of the cap into sealing interface with the rim of the container cup to prevent liquid leakage, and activating the control unit. As the cleaning and disinfecting process progresses, the hydrogen peroxide ($H_2O_2$) in the lens care solution is broken down into liquid water ($H_2O$) and oxygen gas ($O_2$). The released oxygen gas generates a positive pressure differential within the contained volume of the system, relative to the external atmosphere. When this internal pressure reaches a threshold pressure, the top panel of the cap flexes or deforms, disengaging the sealing interface between the lip of the cap and the rim of the container cup. Excess gas is released between the cap lip and cup rim, over the cup rim between the interference ribs, and through the threaded interface between the first and second thread profiles and/or through the unthreaded segments of the split threads. As the gas is released, the pressure drops below the threshold pressure, and the cap flexes back to its undeformed state, sealing the cap lip and cup rim against leakage. The sequence of pressure build-up and release continues until the cleaning and disinfecting process is complete.

After the contact lenses are immersed in the hydrogen peroxide based lens care solution for a predetermined period of immersing time (preferably at least about one hour, more preferably from about 2 hour to about 6 hours, even more preferably from about 3 hours to about 5 hours) sufficient to disinfect the contact lens, the control unit switches on the power and applies a potential to the pair of electrodes, starting the electrochemical neutralization process of hydrogen peroxide. The control unit will turn off the power after a desired period of time sufficient to reduce the concentration of hydrogen peroxide to less than 20 ppm (preferably about 10 ppm or less, more preferably about 5 ppm or less, even more preferably about 1 ppm or less).

After the neutralization of hydrogen peroxide, the lenses may continue to be stored in the container, or removed by unscrewing the cap from the container cup. The apparatus is preferably reusable, and the used lens care solution can be disposed of and the process repeated.

In another aspect, the present invention relates to a lens care apparatus for disinfecting and cleaning contact lenses, comprising: a container for holding a hydrogen peroxide-based lens care solution having a pH of from about 6 to about 8 (preferably from about 6.5 to about 7.5, more preferably from about 6.8 to about 7.2) and comprising from about 0.30% to about 1.4% (preferably from about 0.5% to about 1.2%, more preferably from about 1.0%) by weight of one or more chloride salts (e.g., sodium chloride, potassium chloride, or both) and a tonicity of from about 150 to about 400 mOsm/kg (preferably from about 200 to about 350 mOsm/kg, more preferably from about 250 to about 350 mOsm/kg) as measured by osmolality at 25° C. of the solution according to any known method; one pair of electrodes for electrochemically neutralizing hydrogen peroxide in the hydrogen peroxide-based lens care solution, wherein the pair of electrodes consists of one cathode and one anode having an ion selective membrane (ISM) thereon so as to prevent chloride ions from approaching the electrode to form chlorine and/or hypochlorite and so as to ensure an electrolytically-induced change in pH, designated as $\Delta pH$, being about 1.0 or less (preferably about 0.5 or less), wherein $\Delta pH = |pH_o - pH_f|$ in which $pH_o$ is the initial pH of the lens care solution and $pH_f$ is the final pH of the lens care solution after electrochemical neutralization of hydrogen peroxide; and a control unit operatively connected to the electrodes and to a power source for automatically controlling the electrode polarity and potential of the electrodes, as well as the timing and duration of electrochemically neutralizing of hydrogen peroxide, so that optimum disinfection and cleaning efficacy is obtained, wherein the container comprises a container cup defining an interior chamber accessible through an opening bounded by a rim and for receiving the hydrogen peroxide-based lens care solution, a cap for removable attachment onto the container cup to cover the opening, and a lens holder for retaining the contact lenses immersed in the hydrogen peroxide-based lens care solution in the container cup, wherein the electrodes are located in the interior chamber and immersed in the hydrogen peroxide-based lens care solution when in use. Preferably, the control unit also contains a power pack (with an AC-DC converter or a battery), an automatic switching mechanism, indicator means, or combinations thereof.

In a further aspect, the present invention provides a lens care kit comprising a lens care apparattus of the invention as described above and an aqueous lens care solution comprising including about 0.5% to about 6% by weight (preferably about 2% to about 6% by weight, more preferably from about 3% and about 4% by weight) of hydrogen peroxide.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part or can be combined in any manner and/or used together, as illustrated below:

1. A method for disinfecting and cleaning contact lenses which are suitable for direct insertion into the eye upon completion of disinfection, comprising the steps of:
   (1) immersing a contact lens in an aqueous lens care solution including about 0.5% to about 6% by weight of hydrogen peroxide for a predetermined period of immersing time sufficient to disinfect the contact lens, wherein the aqueous lens care solution comprises from about 0.30% to about 1.4% by weight of one or more chloride salts (e.g., sodium chloride, potassium chloride, or both) and has a pH of from about 6 to about 8 and a tonicity of from about 150 to about 400 mOsm/kg as measured by osmolality at 25° C. of the solution according to any known method; and
   (2) after the predetermined period of immersing time, electrochemically neutralizing said hydrogen peroxide in the aqueous lens care solution with the contact lens immersed therein so as to reduce the concentration of hydrogen peroxide to less than 20 ppm without electrolytic formation of chlorine and/or hypochlorite, wherein the step of electrochemically neutralizing the hydrogen peroxide is carried out by using an anode having a ion selective membrane (ISM) thereon so as to prevent chloride ions from approaching the electrode to form chlorine and/or hypochlorite, wherein the step of electrochemically neutralizing the hydrogen peroxide causes a change in pH, designated as ΔpH, of about 1.0 or less (preferably about 0.5 or less), wherein $\Delta pH = |pH_o - pH_f|$ in which $pH_o$ is the initial pH of the lens care solution and $pH_f$ is the final pH of the lens care solution after electrochemical neutralization of hydrogen peroxide.
2. The method according to embodiment 1, wherein the aqueous lens care solution including about 2% to about 6% by weight (preferably from about 3% and about 4% by weight) of hydrogen peroxide.
3. The method according to embodiment 1 or 2, wherein the predetermined period of immersing time is at least about one hour (preferably from about 2 hour to about 6 hours, more preferably from about 3 hours to about 5 hours).
4. The method according to embodiment 1, 2 or 3, wherein the aqueous lens care solution comprises from about 0.5% to about 1.2% (preferably from about 0.8% to about 1.0%) by weight of one or more chloride salts (e.g., sodium chloride, potassium chloride, or both).
5. The method according to any one of embodiments 1 to 4, wherein the aqueous lens care solution has a pH of from about 6.5 to about 7.5 (preferably from about 6.8 to about 7.2)
6. The method according to any one of embodiments 1 to 5, wherein the aqueous lens care solution has a tonicity of from about 200 to about 350 mOsm/kg (preferably from about 250 to about 350 mOsm/kg) as measured by osmolality at 25° C. of the solution according to any known method.
7. The method according to any one of embodiments 1 to 6, wherein the concentration of hydrogen peroxide in the aqueous lens care solution is reduced electrochemically to about 10 ppm or less (preferably about 5 ppm or less, more preferably about 1 ppm or less) without electrolytic formation of chlorine and/or hypochlorite.
8. The method according to any one of embodiments 1 to 7, wherein ΔpH is about 0.5 or less.
9. The method according to any one of embodiments 1 to 8, wherein the the anode and the cathode are separated by the ISM to facilitate movement of protons between the anode and the cathode.
10. The method according to any one of embodiments 1 to 9, wherein the aqueous lens care solution has a volume in the range of from about 5 ml to about 15 ml (preferably from 7.5 ml to about 12.5 ml, more preferably from about 9 ml to about 11 ml).
11. The method according to any one of embodiments 1 to 10, wherein the aqueous lens care solution further comprises at least one member selected from the group consisting of a polyoxypropylene-polyoxyethylene-polyoxypropylene block copolymer, a poly(oxyethylene)-poly(oxybutylene) block copolymer, a poly(oxyethylene)-poly(oxybutylene) di-block copolymer, a poly(oxyethylene)-poly(oxybutylene)-poly(oxyethylene) tri-block copolymer, a poly(oxybutylene)-poly(oxyethylene)-poly(oxybutylene) tri-block copolymer, a homopolymer of vinylpyrrolidone, a copolymer of vinylpyrrolidone and at least one amino-containing vinylic monomer having 8-15 carbon atoms.
12. The method according to any one of embodiments 1 to 11, wherein the step of electrochemically neutralizing said hydrogen peroxide in the aqueous lens care solution is carried out in a lens care apparatus which comprising: a container for holding a hydrogen peroxide-based lens care solution; one pair of electrodes for electrochemically neutralizing hydrogen peroxide in the hydrogen peroxide-based lens care solution; and a control unit operatively connected to the electrodes and to a power source for automatically controlling the electrode polarity and potential of the electrodes, as well as the timing and duration of electrochemically neutralizing of hydrogen peroxide, so that optimum disinfection and cleaning efficacy is obtained, wherein the container comprises a container cup defining an interior chamber accessible through an opening bounded by a rim and for receiving the hydrogen peroxide-based lens care solution, a cap for removable attachment onto the container cup to cover the opening, and a lens holder for retaining the contact lenses immersed in the hydrogen peroxide-based lens care solution in the container cup, wherein the electrodes are located in the interior chamber and immersed in the hydrogen peroxide-based lens care solution when in use.
13. The method according to embodiment 12, wherein the lens holder comprises one or more closable baskets which open to receive the contact lenses to be disinfected and cleaned and close to retain the lenses during treatment; wherein the electrodes comprise an ion selective membrane (ISM) thereon so as to prevent chloride ions from approaching the electrodes to form undesirable electrolytic products including chlorine and hyperchlorite; and/or wherein the control unit comprises means for operatively connecting the electrodes with the power source and microprocessors/embedded systems for automatically controlling the electrode polarity and potential of the electrodes, as well as the timing and duration of the electrochemical neutralization process.

14. The method according to embodiment 12 or 13, wherein the control unit also contains a power pack (AC-DC converter or DC battery), an automatic switching mechanism, indicator means, or combinations thereof.

15. A lens care apparatus for disinfecting and cleaning contact lenses, comprising:
a container for holding a hydrogen peroxide-based lens care solution having a pH of from about 6 to about 8 (preferably from about 6.5 to about 7.5, more preferably from about 6.8 to about 7.2) and comprising from about 0.30% to about 1.4% (preferably from about 0.5% to about 1.2%, more preferably from about 0.8% to about 1.0%) by weight of one or more chloride salts (e.g., sodium chloride, potassium chloride, or both) and a tonicity of from about 150 to about 400 mOsm/kg (preferably from about 200 to about 350 mOsm/kg, more preferably from about 250 to about 350 mOsm/kg) as measured by osmolality at 25° C. of the solution;
one pair of electrodes for electrochemically neutralizing hydrogen peroxide in the hydrogen peroxide-based lens care solution, wherein the pair of electrodes consists of one cathode and one anode having an ion selective membrane (ISM) thereon so as to prevent chloride ions from approaching the electrode to form chlorine and/or hypochlorite and so as to ensure an electrolytically-induced change in pH, designated as ΔpH, being about 1.0 or less (preferably about 0.5 or less), wherein $\Delta pH = |pH_o - pH_f|$ in which $pH_o$ is the initial pH of the lens care solution and $pH_f$ is the final pH of the lens care solution after electrochemical neutralization of hydrogen peroxide; and
a control unit operatively connected to the electrodes and to a power source for automatically controlling the electrode polarity and potential of the electrodes, as well as the timing and duration of electrochemically neutralizing of hydrogen peroxide, so that optimum disinfection and cleaning efficacy is obtained,
wherein the container comprises a container cup defining an interior chamber accessible through an opening bounded by a rim and for receiving the hydrogen peroxide-based lens care solution, a cap for removable attachment onto the container cup to cover the opening, and a lens holder for retaining the contact lenses immersed in the hydrogen peroxide-based lens care solution in the container cup, wherein the electrodes are located in the interior chamber and immersed in the hydrogen peroxide-based lens care solution when in use.

16. The lens care apparatus according to embodiment 15, wherein the hydrogen peroxide-based lens care solution has a pH of from about 6.5 to about 7.5 (preferably from about 6.8 to about 7.2) and a tonicity of from about 200 to about 350 mOsm/kg (preferably from about 250 to about 350 mOsm/kg) as measured by osmolality at 25° C. of the solution.

17. The lens care apparatus according to embodiment 15 or 16, wherein the hydrogen peroxide-based lens care solution comprises from about 0.5% to about 1.2% (preferably from about 0.8% to about 1.0%) by weight of one or more chloride salts (e.g., sodium chloride, potassium chloride, or both).

18. The lens care apparatus according to any one of embodiments 15 to 17, wherein the lens holder comprises one or more closable baskets, which open to receive the contact lenses to be disinfected and cleaned and close to retain the lenses during treatment.

19. The lens care apparatus according to any one of embodiments 15 to 18, wherein the control unit comprises means for operatively connecting the electrodes with the power source and microprocessors/embedded systems for automatically controlling the electrode polarity and potential of the electrodes, as well as the timing and duration of the electrochemical neutralization process.

20. The lens care apparatus according to any one of embodiments 15 to 19, wherein the control unit comprises a power pack (AC-DC converter or DC battery), an automatic switching mechanism, indicator means, or combinations thereof.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

A 30 ppm of hydrogen peroxide was dissolved in a typical buffer system (0.5% boric acid, 0.05% sodium borate decahydrate, 0.9% sodium acetate) and verified with peroxide strips. A pair of platinum wires was immersed in the solution. A 4 V potential was applied, and the peroxide levels were monitored by using peroxide strips. After 30 minutes at 10 mA, the approximate peroxide level was approximately 2 ppm. By calculation, the reaction to reduce 10 ml of a 3% hydrogen peroxide solution (typically found in ClearCare), the peroxide can be reduced to safe conditions (<10 ppm) on eye by applying 150 mA for 4 hours.

What is claimed is:
1. A method for disinfecting and cleaning contact lenses which are suitable for direct insertion into the eye upon completion of disinfection, comprising the steps of:
(1) immersing a contact lens in an aqueous lens care solution including about 0.5% to about 6% by weight of hydrogen peroxide for a predetermined period of immersing time of at least about one hour to disinfect the contact lens, wherein the aqueous lens care solution comprises from about 0.30% to about 1.4% by weight of one or more chloride salts and has a pH of from about 6 to about 8 and a tonicity of from about 150 to about 400 mOsm/kg as measured by osmolality at 25° C. of the solution according to any known method; and
(2) after the predetermined period of immersing time, electrochemically neutralizing said hydrogen peroxide in the aqueous lens care solution with the contact lens immersed therein so as to reduce the concentration of hydrogen peroxide to less than 20 ppm without electrolytic formation of chlorine and/or hypochlorite, wherein the step of electrochemically neutralizing the hydrogen peroxide is carried out by using one pair of electrodes, wherein the pair of electrodes consists of one cathode and one anode having an ion selective membrane thereon so as to prevent chloride ions from approaching the anode to form chlorine and/or hypochlorite, wherein the step of electrochemically neutralizing the hydrogen peroxide causes a change in pH, designated as $\Delta$pH, of about 1.0 or less, wherein $\Delta pH = |pH_o - pH_f|$ in which $pH_o$ is the initial pH of the lens care solution and $pH_f$ is the final pH of the lens care solution after electrochemical neutralization of hydrogen peroxide.

2. The method claim 1, wherein the anode and the cathode are separated by the ion selective membrane to facilitate movement of protons between the anode and the cathode.

3. The method claim 1, wherein the aqueous lens care solution has a volume in the range of from about 5 ml to about 15 ml.

4. The method of claim 1, wherein the aqueous lens care solution comprises at least one member selected from the group consisting of a polyoxypropylene-polyoxyethylene-polyoxypropylene block copolymer, a poly(oxyethylene)-poly(oxybutylene) block copolymer, a poly(oxyethylene)-poly(oxybutylene) di-block copolymer, a poly(oxyethylene)-poly(oxybutylene)-poly(oxyethylene) tri-block copolymer, a poly(oxybutylene)-poly(oxyethylene)-poly(oxybutylene) tri-block copolymer, a homopolymer of vinylpyrrolidone, a copolymer of vinylpyrrolidone and at least one amino-containing vinylic monomer having 8-15 carbon atoms.

5. The method of claim 1, wherein the aqueous lens care solution comprises from about 0.5% to about 1.2% by weight of sodium chloride or potassium chloride or both.

6. The method of claim 1, wherein the step of electrochemically neutralizing said hydrogen peroxide in the aqueous lens care solution is carried out in a lens care apparatus which comprises: a container for holding a hydrogen peroxide-based lens care solution; one pair of electrodes for electrochemically neutralizing hydrogen peroxide in the hydrogen peroxide-based lens care solution; and a control unit operatively connected to the electrodes and to a power source for automatically controlling the electrode polarity and potential of the electrodes, as well as the timing and duration of electrochemically neutralizing of hydrogen peroxide, so that optimum disinfection and cleaning efficacy is obtained, wherein the container comprises a container cup defining an interior chamber accessible through an opening bounded by a rim and for receiving the hydrogen peroxide-based lens care solution, a cap for removable attachment onto the container cup to cover the opening, and a lens holder for retaining the contact lenses immersed in the hydrogen peroxide-based lens care solution in the container cup, wherein the electrodes are located in the interior chamber and immersed in the hydrogen peroxide-based lens care solution when in use.

7. The method of claim 6, wherein the lens holder comprises one or more closable baskets which open to receive the contact lenses to be disinfected and cleaned and close to retain the lenses during treatment; wherein the electrodes comprise an ion selective membrane thereon so as to prevent chloride ions from approaching the electrodes to form undesirable electrolytic products including chlorine and hyperchlorite; and/or wherein the control unit comprises an electronic circuitry for operatively connecting the electrodes with the power source and microprocessors and/or embedded systems for automatically controlling the electrode polarity and potential of the electrodes, as well as the timing and duration of the electrochemical neutralization process.

8. The method of claim 6, wherein the control unit also contains a power pack, an automatic switching mechanism, indicator, or combinations thereof.

9. The method of claim 2, wherein the aqueous lens care solution has a volume in the range of from about 5 ml to about 15 ml.

10. The method of claim 9, wherein the aqueous lens care solution comprises at least one member selected from the group consisting of a polyoxypropylene-polyoxyethylene-polyoxypropylene block copolymer, a poly(oxyethylene)-poly(oxybutylene) block copolymer, a poly(oxyethylene)-poly(oxybutylene) di-block copolymer, a poly(oxyethylene)-poly(oxybutylene)-poly(oxyethylene) tri-block copolymer, a poly(oxybutylene)-poly(oxyethylene)-poly(oxybutylene) tri-block copolymer, a homopolymer of vinylpyrrolidone, a copolymer of vinylpyrrolidone and at least one amino-containing vinylic monomer having 8-15 carbon atoms.

11. The method of claim 10, wherein the aqueous lens care solution comprises from about 0.5% to about 1.2% by weight of sodium chloride or potassium chloride or both.

12. The method of claim 11, wherein the step of electrochemically neutralizing said hydrogen peroxide in the aqueous lens care solution is carried out in a lens care apparatus which comprises: a container for holding a hydrogen peroxide-based lens care solution; one pair of electrodes for electrochemically neutralizing hydrogen peroxide in the hydrogen peroxide-based lens care solution; and a control unit operatively connected to the electrodes and to a power source for automatically controlling the electrode polarity and potential of the electrodes, as well as the timing and duration of electrochemically neutralizing of hydrogen peroxide, so that optimum disinfection and cleaning efficacy is obtained, wherein the container comprises a container cup defining an interior chamber accessible through an opening bounded by a rim and for receiving the hydrogen peroxide-based lens care solution, a cap for removable attachment onto the container cup to cover the opening, and a lens holder for retaining the contact lenses immersed in the hydrogen peroxide-based lens care solution in the container cup, wherein the electrodes are located in the interior chamber and immersed in the hydrogen peroxide-based lens care solution when in use.

13. The method of claim 12, wherein the lens holder comprises one or more closable baskets which open to receive the contact lenses to be disinfected and cleaned and close to retain the lenses during treatment; wherein the electrodes comprise an ion selective membrane thereon so as to prevent chloride ions from approaching the electrodes to form undesirable electrolytic products including chlorine and hyperchlorite; and/or wherein the control unit comprises an electronic circuitry for operatively connecting the electrodes with the power source and microprocessors and/or embedded systems for automatically controlling the electrode polarity and potential of the electrodes, as well as the timing and duration of the electrochemical neutralization process.

14. The method of claim 12, wherein the control unit also contains a power pack, an automatic switching mechanism, indicator, or combinations thereof.

15. The method of claim 2, wherein the aqueous lens care solution comprises at least one member selected from the group consisting of a polyoxypropylene-polyoxyethylene-polyoxypropylene block copolymer, a poly(oxyethylene)-poly(oxybutylene) block copolymer, a poly(oxyethylene)-poly(oxybutylene) di-block copolymer, a poly(oxyethylene)-poly(oxybutylene)-poly(oxyethylene) tri-block copolymer, a poly(oxybutylene)-poly(oxyethylene)-poly(oxybutylene) tri-block copolymer, a homopolymer of vinylpyrrolidone, a copolymer of vinylpyrrolidone and at least one amino-containing vinylic monomer having 8-15 carbon atoms.

16. The method of claim 15, wherein the aqueous lens care solution comprises from about 0.5% to about 1.2% by weight of sodium chloride or potassium chloride or both.

17. The method of claim 16, wherein the step of electrochemically neutralizing said hydrogen peroxide in the aqueous lens care solution is carried out in a lens care apparatus which comprises: a container for holding a hydrogen peroxide-based lens care solution; one pair of electrodes for electrochemically neutralizing hydrogen peroxide in the hydrogen peroxide-based lens care solution; and a control unit operatively connected to the electrodes and to a power source for automatically controlling the electrode polarity and potential of the electrodes, as well as the timing and duration of electrochemically neutralizing of hydrogen peroxide, so that optimum disinfection and cleaning efficacy is obtained, wherein the container comprises a container cup defining an interior chamber accessible through an opening bounded by a rim and for receiving the hydrogen peroxide-based lens care solution, a cap for removable attachment onto the container cup to cover the opening, and a lens holder for retaining the contact lenses immersed in the hydrogen peroxide-based lens care solution in the container cup, wherein the electrodes are located in the interior chamber and immersed in the hydrogen peroxide-based lens care solution when in use.

18. The method of claim 17, wherein the lens holder comprises one or more closable baskets which open to receive the contact lenses to be disinfected and cleaned and close to retain the lenses during treatment; wherein the electrodes comprise an ion selective membrane thereon so as to prevent chloride ions from approaching the electrodes to form undesirable electrolytic products including chlorine and hyperchlorite; and/or wherein the control unit comprises an electronic circuitry for operatively connecting the electrodes with the power source and microprocessors and/or embedded systems for automatically controlling the electrode polarity and potential of the electrodes, as well as the timing and duration of the electrochemical neutralization process.

19. The method of claim 18, wherein the control unit also contains a power pack, an automatic switching mechanism, indicator, or combinations thereof.

* * * * *